United States Patent [19]
Niewöhner et al.

[11] Patent Number: 5,861,396
[45] Date of Patent: Jan. 19, 1999

[54] PURIN-6-ONE DERIVATIVES

[75] Inventors: Ulrich Niewöhner, Wermelskirchen; Erwin Bischoff, Wuppertal; Joachim Hütter, Wuppertal; Elisabeth Perzborn, Wuppertal; Helmuth Schütz, Wuppertal, all of Germany

[73] Assignee: Bayer Aktiengesellschaft, Leverkusen, Germany

[21] Appl. No.: 739,742

[22] Filed: Oct. 30, 1996

[30] Foreign Application Priority Data

Nov. 6, 1995 [DE] Germany .................. 195 41 264.8

[51] Int. Cl.$^6$ .................. C07D 473/30; A61K 31/52
[52] U.S. Cl. .................. 514/234.2; 514/262; 544/118; 544/265
[58] Field of Search .................. 544/265, 118; 514/234.2, 262

[56] References Cited

U.S. PATENT DOCUMENTS

| | | | |
|---|---|---|---|
| 4,451,478 | 5/1984 | Simon et al. | 544/277 |
| 5,298,621 | 3/1994 | Marzi | 544/265 |

FOREIGN PATENT DOCUMENTS

| | | |
|---|---|---|
| 0 178 178 A2 | 4/1986 | European Pat. Off. . |
| WO 88/03923 | 11/1987 | WIPO . |

OTHER PUBLICATIONS

Beavo et al., Trends in Pharmacol. Sci. 11, 150–155 (1990).
Logemann et al., Chemistry and Industry 1980 (13), 541–542.
Krepski et al., Synthesis, 1986, 301–303.
Hoey et al., Biochemical Pharmacology. vol. 40, 193–202 (1990).
Steif et al., World Journal Urology 1990, S. 233–236.
Lane, Synthesis, 1975 135–146.
Birkett et al., Synthesis, 1991, 157–159.
Shaw et al., J. Chem.Soc. 1959, 1644–1655.

*Primary Examiner*—Mark L. Berch
*Attorney, Agent, or Firm*—Sprung Kramer Schaefer & Briscoe

[57] ABSTRACT

Purin-6-one derivatives are prepared by acylating appropriately substituted imidazole carboxamides and then cyclizing to give the purines. The purin-6-one derivatives are suitable as active compounds in medicaments, in particular for the treatment of cardiovascular disorders, disorders of the vascular system and of the urogenital system.

6 Claims, No Drawings

PURIN-6-ONE DERIVATIVES

The present invention relates to purin-6-one derivatives, a process for their preparation and their use in medicaments, in particular for the treatment of cardiovascular and cerebrovascular disorders, peripheral vascular disorders and diseases of the urogenital system.

Phosphodiesterases (PDEs) play an essential role in the regulation of the intracellular cGMP and cAMP level. Of the phosphodiesterase isoenzyme groups PDE I to PDE V described until now [nomenclature according to Beavo and Reifsnyder (cf Beavo, J. A. and Reifsnyder, D. H.: Trends in Pharmacol. Sci 11, 150–155 (1990))], the Ca calmodulin-activated PDE I, the cGMP-stimulable PDE II and the cGMP-specific PDE V are essentially responsible for the metabolism of cGMP. On account of the differing distribution of these cGMP-metabolizing PDEs in the tissue, selective inhibitors, according to the tissue distribution of the corresponding isoenzyme, should raise the cGMP level in the corresponding tissue. This can lead to a specific antiaggregatory, antispastic, vasodilating and/or antiarrhythmic action.

The present invention now relates to purin-6-one derivatives of the general formula (I)

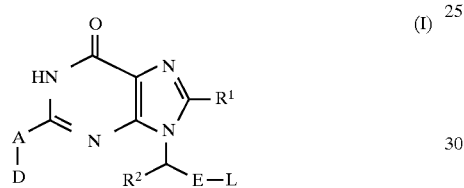

in which $R^1$ represents hydrogen or straight-chain or branched alkyl having up to 8 carbon atoms, $R^2$ represents straight-chain or branched acyl having up to 4 carbon atoms, or represents straight-chain or branched alkyl having up to 8 carbon atoms, which is optionally substituted by hydroxyl, azido or by a group of the formula —$NR^3R^4$ or —$OSO_2R^5$, in which $R^3$ and $R^4$ are identical or different and denote cycloalkyl having 3 to 6 carbon atoms, hydrogen, formyl or straight-chain or branched alkyl having up to 6 carbon atoms, which is optionally substituted by hydroxyl, carboxyl or by straight-chain or branched alkoxy or alkoxycarbonyl each having up to 6 carbon atoms or by a group of the formula —$(CO)_a$—$NR^6R^7$, in which a denotes a number 0 or 1

$R^6$ and $R^7$ are identical or different and denote hydrogen, formyl, hydroxyl, phenyl or straight-chain or branched alkyl having up to 6 carbon atoms, which is optionally substituted by hydroxyl or by straight-chain or branched alkoxy having up to 5 carbon atoms, or $R^3$ and/or $R^4$ denote straight-chain or branched alkoxycarbonyl having up to 6 carbon atoms, carboxyl or straight-chain or branched acyl having up to 6 carbon atoms, which is optionally substituted by hydroxyl or straight-chain or branched alkoxy having up to 4 carbon atoms or $R^3$ and/or $R^4$ denote a radical of the formula —$(CO)_b$—T—$NR^8R^9$, —CO—$R^{10}$, —$SO_2R^{11}$ or —$SO_2NR^{12}R^{13}$, in which b has the meaning of a indicated above and is identical to or different from this T denotes straight-chain or branched alkyl having up to 5 carbon atoms or if b≠0 can also denote a bond, $R^8$ and $R^9$ have the meaning of $R^6$ and $R^7$ indicated above and are identical to or different from this $R^{10}$ denotes a saturated, partially unsaturated or unsaturated 5- to 7-membered heterocycle having up to 3 heteroatoms from the series S, N and/or O, which can optionally also be substituted via the N function, by straight-chain or branched alkyl, alkoxy or alkoxycarbonyl each having up to 4 carbon atoms, carboxyl, benzyloxycarbonyl or hydroxyl, $R^{11}$ denotes straight-chain or branched alkyl having up to 5 carbon atoms, benzyl or phenyl, $R^{12}$ and $R^{13}$ are identical or different and denote hydrogen, phenyl or straight-chain or branched alkyl having up to 6 carbon atoms, or $R^3$ and $R^4$, together with the nitrogen atom, form a 5- or 6-membered saturated, partially unsaturated or unsaturated heterocycle which can contain up to 3 heteroatoms from the series N, S and/or O or a radical —$NR^{14}$, and which is optionally substituted by carbonyl, by straight-chain or branched alkoxycarbonyl having up to 5 carbon atoms or by straight-chain or branched alkyl having up to 5 carbon atoms, which for its part can be substituted by hydroxyl, carboxyl or by straight-chain or branched acyl, alkoxy or alkoxycarbonyl each having up to 6 carbon atoms, in which $R^{14}$ denotes hydrogen, carbonyl or straight-chain or branched alkyl or alkoxycarbonyl each having up to 5 carbon atoms, and $R^5$ denotes phenyl or straight-chain or branched alkyl having up to 5 carbon atoms, A represents a straight-chain or branched alkylene or alkenylene chain each having up to 6 carbon atoms, D and L are identical or different and represent aryl having 6 to 10 carbon atoms or a 5- to 7-membered aromatic, optionally benzo-fused heterocycle having up to 3 heteroatoms from the series S, N and/or O, each of which is optionally substituted up to 3 times identically or differently by halogen, hydroxyl, nitro, trifluoromethyl, carboxyl, straight-chain or branched alkyl, alkoxy or alkoxycarbonyl each having up to 6 carbon atoms or by a group of the formula —$(V_c$—$NR^{15}R^{16}$ and/or —$OR^{17}$, in which c denotes a number 0 or 1, V denotes a radical of the formula —CO or —$SO_2$, $R^{15}$ and $R^{16}$ are identical or different and have the meaning of $R^3$ and $R^4$ indicated above, $R^{17}$ denotes hydrogen, straight-chain or branched alkenyl having up to 8 carbon atoms or straight-chain or branched alkyl having up to 8 carbon atoms, which is optionally substituted up to 3 times identically of differently by hydroxyl, carboxyl or straight-chain or branched alkoxycarbonyl having up to 5 carbon atoms, and/or the cycles are optionally substituted by aryl having 6 to 10 carbon atoms or by a 5- to 7-membered aromatic, optionally benzo-fused heterocycle having up to 3 heteroatoms from the series S, N and/or O, each of which for its part is optionally substituted up to 2 times identically or differently by halogen, hydroxyl, nitro, carboxyl, trifluoromethyl or by straight-chain or branched alkyl, alkoxy or alkoxycarbonyl each having up to 5 carbon atoms or by a group of the formula $(V')_d$—$NR^{18}R^{19}$, in which d has the meaning of a indicated above and is identical to or different from this, $R^{18}$ and $R^{19}$ have the meaning of $R^3$ and $R^4$ indicated above and are identical to or different from this, V' has the meaning of V indicated above and is identical or different from this, and/or the ring systems mentioned under D are optionally substituted by straight-chain or branched acyl having up to 5 carbon atoms, which is optionally substituted by hydroxyl, straight-chain or branched alkoxy having up to 5 carbon atoms or by a group of the formula —$NR^{20}R^{21}$, in which $R^{20}$ and $R^{21}$ are identical or different and have the meaning of $R^3$ and $R^4$ indicated above, or D represents a radical of the formula

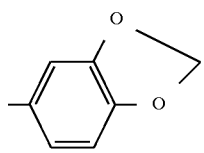

and

E represents a radical of the formula —$CH_2$—Y—Z—, in which

Y denotes a bond or an oxygen or sulphur atom or the —NH group,

Z denotes a straight-chain or branched alkylene chain having up to 5 carbon atoms, and their tautomers and salts.

The substances according to the invention can also exist as salts. In the context of the invention physiologically acceptable salts are preferred.

Physiologically acceptable salts can be salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric. acid, tartaric acid, lactic acid, benzoic acid or methanesulphonic acid, ethanesulphonic acid, phenylsulphonic acid, toluenesulphonic acid or naphthalenedisulphonic acid.

The compounds of the general formula (I) according to the invention can occur in various stereochemical forms which either behave as image and mirror image (enantiomers), or which do not behave as image and mirror image (diastereomers). The invention relates both to the antipodes and to the racemic forms as well as the diastereomer mixtures. Like the diastereomers, racemic forms can be separated into the stereoisomerically uniform constituents in a known manner.

Heterocycle in the content of the invention in general represents a partially unsaturated, saturated or unsaturated 5- to 7-membered, preferably 5- to 6-membered, heterocycle which can contain up to 3 heteroatoms from the series S, N and/or O. Examples which may be mentioned are: pyridyl, pyrrolidinyl, piperazinyl, thienyl, indolyl, furyl, pyrrolyl, thiazolyl, oxazolyl, imidazolyl, morpholinyl or piperidyl. Pyridyl, thienyl, indolyl, furyl, piperazinyl, morpholinyl and pyrrolidinyl are preferred.

Preferred compounds of the general formula (I) are those in which $R^1$ represents hydrogen or straight-chain or branched alkyl having up to 6 carbon atoms, $R^2$ represents straight-chain or branched acyl having up to 6 carbon atoms, or represents straight-chain or branched alkyl having up to 6 carbon atoms, which is optionally substituted by hydroxyl, azido or by a group of the formula —$NR^3R^4$ or O—$SO_2$—$R^5$, in which $R^3$ and $R^4$ are identical or different and denote cyclopentyl, cyclohexyl, hydrogen, formyl or straight-chain or branched alkyl having up to 5 carbon atoms, which is optionally substituted by hydroxyl, carboxyl or by straight-chain or branched alkoxy or alkoxycarbonyl each having up to 5 carbon atoms or by a group of the formula —$(CO)_a$—$NR^6R^7$, in which a denotes a number 0 or 1, $R^6$ and $R^7$ are identical or different and denote hydrogen, formyl, hydroxyl, phenyl or straight-chain or branched alkyl having up to 5 carbon atoms, which is optionally substituted by hydroxyl or by straight-chain or branched alkoxy having up to 4 carbon atoms, or $R^3$ and/or $R^4$ denote straight-chain or branched alkoxycarbonyl having up to 1 carbon atoms, carboxyl or straight-chain or branched acyl having up to 5 carbon atoms, which is optionally substituted by hydroxyl or straight-chain or branched alkoxy having up to 3 carbon atoms or $R^3$ and/or $R^4$ denote a radical of the formula —$(CO)_b$—T—$NR^8R^9$, —CO—$R^{10}$, —$SO_2R^{11}$ or —$SO_2NR^{12}R^{13}$, in which b has the meaning of a indicated above and is identical to or different from this T denotes straight-chain or branched alkyl having up to 4 carbon atoms or if b≠0 can also denote a bond, $R^8$ and $R^9$ have the meaning of $R^6$ and $R^7$ indicated above and are identical to or different from this $R^{10}$ denotes morpholinyl, imidazolyl, pyridyl, piperazinyl, piperidinyl or pyrrolidinyl, each of which can optionally be substituted, also via the N function, by straight-chain or branched alkyl, alkoxy or alkoxycarbonyl each having up to 3 carbon atoms, carboxyl, benzyloxycarbonyl or hydroxyl, $R^{11}$ denotes straight-chain or branched alkyl having up to 4 carbon atoms, benzyl or phenyl, $R^{12}$ and $R^{13}$ are identical or different and denote hydrogen, phenyl or straight-chain or branched alkyl having up to 5 carbon atoms, or $R^3$ and $R^4$, together with the nitrogen atom, form a pyrrolidinyl, morpholinyl, imidazolyl, piperidinyl or piperazinyl ring, each of which, optionally also via the nitrogen function, can be substituted by straight-chain or branched alkoxycarbonyl having up to 4 carbon atoms, carboxyl, or by straight-chain or branched alkyl having up to 4 carbon atoms, which for its part can be substituted by carboxyl, hydroxyl or by straight-chain or branched acyl, alkoxy or alkoxycarbonyl each having up to 4 carbon atoms, and $R^5$ denotes phenyl or straight-chain or branched alkyl having up to 4 carbon atoms, A represents a straight-chain or branched alkylene or alkenylene chain each having up to 5 carbon atoms, D and L are identical or different and represent phenyl, naphthyl, pyridyl, pyridinyl, thienyl, indolyl or furyl, each of which is optionally substituted up to 3 times identically or differently by fluorine, chlorine, bromine, trifluoromethyl, nitro, carboxyl, straight-chain or branched alkyl or alkoxycarbonyl each having up to 5 carbon atoms or by a group of the formula $-(V)_c NR^{15}R^{16}$ and/or $-OR^{17}$, in which c denotes a number 0 or 1, V denotes a radical of the formula $-CO$ or $-SO_2$, $R^{15}$ and $R^{16}$ are identical or different and have the meaning of $R^3$ and $R^4$ indicated above, $R^{17}$ denotes hydrogen, straight-chain or branched alkenyl having up to 6 carbon atoms or straight-chain or branched alkyl having up to 6 carbon atoms, which is optionally substituted up to 2 times identically or differently by hydroxyl, carboxyl or by straight-chain or branched alkoxycarbonyl having up to 4 carbon atoms, and/or the cycles are optionally substituted by naphthyl, phenyl, pyridyl, indolyl, thienyl, furyl, pyridazinyl, pyridyl, pyrryl or pyrimidyl, each of which for its part is optionally substituted by fluorine, chlorine, bromine, hydroxyl, nitro, carboxyl, trifluoromethyl or by straight-chain or branched alkyl, alkoxy or alkoxycarbonyl each having up to 3 carbon atoms or by a group of the formula $-(V')_d NR^{18}R^{19}$, in which d has the meaning of a indicated above and is identical to or different from this, V' has the meaning of V indicated above and is identical to or different from this, $R^{18}$ and $R^{19}$ have the meaning of $R^3$ and $R^4$ indicated above, and/or the ring systems mentioned under D are optionally substituted by straight-chain or branched acyl having up to 4 carbon atoms, which is optionally substituted by hydroxyl, straight-chain or branched alkoxy having up to 4 carbon atoms or by a group of the formula $-NR^{20}R^{21}$, in which $R^{20}$ and $R^{21}$ are identical or different and have the meaning of $R^3$ and $R^4$ indicated above, or D represents a radical of the formula

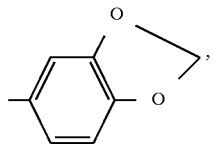

E represents a radical of the formula. $-CH_2-Y-Z-$, in which

Y denotes a bond or an oxygen or sulphur atom or the $-NH$ group,

Z denotes a straight-chain or branched alkylene chain having up to 4 carbon atoms, and their tautomers and salts.

Particularly preferred compounds of the general formula (I) are those in which $R^1$ represents hydrogen or straight-chain or branched alkyl having up to 4 carbon atoms, $R^2$ represents straight-chain or branched acyl having up to 5 carbon atoms, or represents straight-chain or branched alkyl having up to 5 carbon atoms, which is optionally substituted by hydroxyl, azido or by a group of the formula $-NR^3R^4$ or $O-SO_2R^5$, in which $R^3$ and $R^4$ are identical or different and denote cyclopentyl, hydrogen, formyl or straight-chain or branched alkyl having up to 4 carbon atoms, which is optionally substituted by hydroxyl, carboxyl or by straight-chain or branched alkoxy or each alkoxycarbonyl having up to 3 carbon atoms or by a group of the formula $-(CO)_a-NR^6R^7$, in which a denotes a number 0 or 1, $R^6$ and $R^7$ are identical or different and denote hydrogen, formyl, hydroxyl or straight-chain or branched alkyl having up to 3 carbon atoms, which is optionally substituted by hydroxyl, or by straight-chain or branched alkoxy having up to 3 carbon atoms, or $R^3$ and/or $R^4$ denote straight-chain or branched alkoxycarbonyl having up to 3 carbon atoms, carboxyl or straight-chain or branched acyl having up to 3 carbon atoms, which is optionally substituted by hydroxyl, methoxy or ethoxy or $R^3$ and/or $R^4$ denote a radical of the formula $-(CO)_b-T-NR^8R^9$, $-CO-R^{10}$, $-SO_2R^{11}$ or $-SO_2NR^{12}R^{13}$, in which b has the meaning of a indicated above and is identical to or different from this T denotes straight-chain or branched alkyl having up to 3 carbon atoms or if b≠0 can also denote a bond, $R^8$ and $R^9$ have the meaning of $R^6$ and $R^7$ indicated above and are identical to or different from this $R^{10}$ denotes morpholinyl, piperidinyl, piperazinyl or pyrrolidinyl, each of which can optionally also be substituted via the N function, by straight-chain or branched alkyl, alkoxy or alkoxycarbonyl each having up to 3 carbon atoms, benzyloxycarbonyl, carboxyl or hydroxyl, $R^{11}$ denotes straight-chain or branched alkyl having up to 3 carbon atoms, benzyl or phenyl, $R^{12}$ and $R^{13}$ are identical or different and denote hydrogen or straight-chain or branched alkyl having up to 4 carbon atoms, or $R^3$ and $R^4$, together with the nitrogen atom, form a pyrrolidinyl, morpholinyl, imidazolyl, piperidinyl or piperazinyl ring, each of which, optionally also via the nitrogen function, can be substituted by straight-chain or branched alkyl or alkoxycarbonyl each having up to 3 carbon atoms or carboxyl or by straight-chain or branched alkyl having up to 3 carbon atoms, which for its part can be substituted by carboxyl, hydroxyl or by straight-chain or branched acyl, alkoxy or alkoxycarbonyl each having up to 3 carbon atoms and $R^5$ denotes phenyl or straight-chain or branched alkyl having up to 3 carbon atoms, A represents an ethenyl (-vinyl) or an alkylene chain having up to 4 carbon atoms, in which D and L are identical or different and represent phenyl, naphthyl, furyl, thienyl, indolyl or pyridyl, each of which is optionally substituted up to 2 times identically or differently by fluorine, chlorine, bromine, nitro, carboxyl, trifluoromethyl, straight-chain or branched alkyl or alkoxycarbonyl each having up to 4 carbon atoms or by a group of the formula $-(V)_c NR^{15}R^{16}$ and/or $-OR^{17}$, in which c denotes a number 0 or 1, V denotes a radical of the formula $-CO$ or $-SO_2$, $R^{15}$ and $R^{16}$ are identical or different and have the meaning of $R^3$ and $R^4$ indicated above, $R^{17}$ denotes hydrogen, straight-chain or branched alkenyl having up to 4 carbon atoms or straight-chain or branched alkyl having up to 4 carbon atoms, which is optionally substituted up to 2 times identically or differently by hydroxyl, carboxyl or by straight-chain or branched alkoxycarbonyl having up to 3 carbon atoms and/or the cycles are optionally substituted by phenyl, pyrimidyl, pyridazinyl, pyridyl, thienyl or furyl, each of which for its part is optionally substituted by fluorine, chlorine, bromine, hydroxyl, nitro, carboxyl, trifluoromethyl or by straight-chain or branched alkyl, alkoxy or alkoxycarbonyl each having up to 3 carbon atoms or by a group of the formula $-(V')_d NR^{18}R^{19}$, in which d has the meaning of a indicated above and is identical to or different from this, V' has the meaning of V indicated above and is identical to or different from this, $R^{18}$ and $R^{19}$ have the meaning of $R^3$ and $R^4$ indicated above, and/or D is optionally substituted by straight-chain or branched acyl having up to 3 carbon atoms, which is optionally substituted by hydroxyl, straight-chain or branched alkoxy having up to 3 carbon atoms or by a group of the formula $-NR^{20}R^{21}$, in which $R^{20}$ and $R^{21}$ are identical or different and have the meaning of $R^3$ and $R^4$ indicated above, D represents a radical of the formula

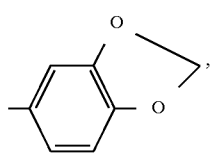

E represents a radical of the formula $-CH_2-Y-Z-$, in which

Y denotes a bond or an oxygen or sulphur atom or the $-NH$ group,

Z denotes an alkylene chain having up to 4 carbon atoms and their tautomers and salts.

Very particularly preferred compounds of the general formula (I) are those in which L represents phenyl which is optionally substituted by fluorine, chlorine, methyl or methoxy, $R^1$ represents hydrogen, methyl or ethyl and $R^2$ represents $CH_3$, isopropyl or the groups

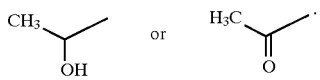

Processes for the preparation of the compounds of the general formula (I) according to the invention have additionally been found, characterized in that

[A] first compounds of the general formula (II)

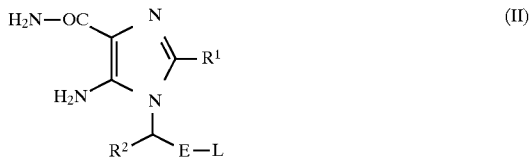

in which $R^1$, $R^2$, E and L have the meaning indicated, are converted by reaction with compounds of the general formula (III)

in which

A and D have the meaning indicated, in inert solvents and in the presence of a base, into the compounds of the general formula (IV)

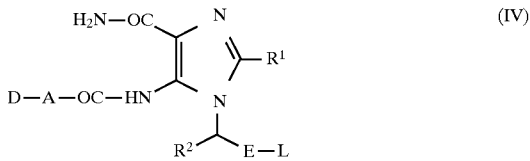

in which

A, D, E, L, $R^1$ and $R^2$ have the meaning indicated, and in a second step these are cyclized in inert solvents and in the presence of a base, or

[B] compounds of the general formula (II) are directly reacted with compounds of the general formula (V)

in which

D and A have the meaning indicated above and $R^{22}$ represents $C_1$–$C_4$-alkyl in alcohols and in the presence of a base, and, if appropriate, the substituents mentioned under $R^2$ are introduced or derivatized by subsequent reactions such as acylation, oxidation, substitution and/or reduction, and the substituents mentioned under D and L are likewise introduced and/or varied by customary methods.

The process according to the invention can be illustrated by way of example by the following reaction scheme:

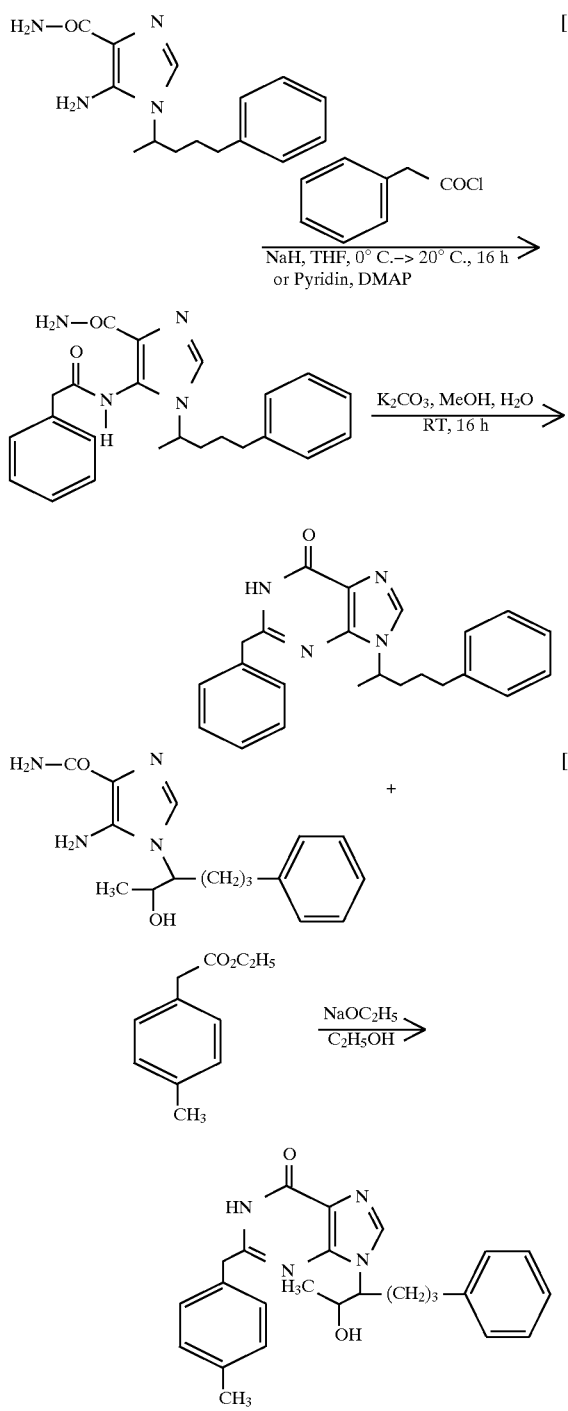

Suitable solvents for the first step of process [A] are inert organic solvents which do not change under the reaction conditions. These preferably include ethers such as, for example, diethyl ether, dioxane, tetrahydrofuran or glycol dimethyl ether or toluene, hexamethylphosphoramide and pyridine. Of course, it is possible to employ mixtures of the solvents. Tetrahydrofuran, toluene and pyridine are particularly preferred.

Suitable bases are in general alkali metal hydrides or alkoxides, such as, for example, sodium hydride or potassium tert-butoxide, or cyclic amines, such as, for example, piperidine, pyridine, dimethylarninopyridine or $C_1$–$C_4$-alkylamines, such as, for example, triethylamine. Sodium hydride, pyridine, and/or dimethylaminopyridine are preferred.

The base is in general employed in an amount of from 1 mol to 4 mol, preferably from 1.2 mol to 3 mol, in each case relative to 1 mol of the compounds of the general formula (II).

The reaction temperature can in general be varied within a relatively wide range. In general, the reaction is carried out in a range from –20° C. to 200° C., preferably from 0° C. to 100° C.

In one variant, the reaction is carried out in pyridine to which a catalytic amount of DMAP is added. If appropriate, toluene can additionally be added.

Suitable solvents for the cyclization are the customary organic solvents. These preferably include alcohols such as methanol, ethanol, propanol, isopropanol or butanol, or ethers such as tetrahydrofuran or dioxane, or dimethylformamide or dimethyl sulphoxide. Particularly preferably, alcohols such as methanol, ethanol, propanol or isopropanol are used. It is also possible to employ mixtures of the solvents mentioned.

Suitable bases for the cyclization are the customary inorganic bases. These preferably include alkali metal hydroxides or alkaline earth metal hydroxides such as, for example, sodium hydroxide, potassium hydroxide or barium hydroxide, or alkali metal carbonates such as sodium or potassium carbonate or sodium hydrogen carbonate, or alkali metal alkoxides such as sodium methoxide, sodium ethoxide, potassium methoxide, potassium ethoxide or potassium tert-butoxide. Potassium carbonate and sodium hydroxide are particularly preferred.

When carrying out the cyclization, the base is in general employed in an amount of from 2 to 6 mol, preferably from 3 to 5 mol, relative to 1 mol of the compounds of the formula (IV).

The cyclization is in general carried out in a temperature range from 0° C. to 160° C., preferably at the boiling point of the respective solvent.

The cyclization is in general carried out at normal pressure. However, it is also possible to carry out the process at elevated pressure or at reduced pressure (e.g. in a range from 0.5 to 5 bar).

Suitable solvents for process [B] are the alcohols mentioned above, ethanol being preferred.

Suitable bases for process [B] are alkoxides, such as, for example, sodium methoxide, ethoxide or isopropoxide or potassium tert-butoxide. Sodium ethoxide is preferred.

The base is employed in an amount of from 2 mol to 8 mol, preferably from 3 mol to 6 mol, in each case relative to 1 mol of the compounds of the general formula (II).

The ketones are prepared by known methods (Swem oxidation or Colling oxidation) starting from the corresponding hydroxy compounds.

The variations of the substituents on the aromatics are carried out according to known methods.

The enantiomerically pure compounds are accessible according to customary methods, for example by chromatography of the racemic compounds of the general formula (I) on chiral phases or by the use of chiral starting compounds.

The compounds of the general formula (II) are new and can be prepared, for example, by reacting 2-amino-2-cyanoacetamide of the formula (VI)

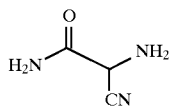 (VI)

with compounds of the general formula (VII)

$R^1C(OC_2H_5)_3$ (VII)

in which
$R^1$ has the meaning indicated above,
and in a second step reacting with compounds of the general formula (VIII)

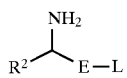 (VIII)

in which
$R^2$, E and L have the meaning indicated,
in inert solvents.

Suitable solvents for the individual steps of the processes are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, dimethylformamide, hexamethylphosphoramide, acetonitrile, acetone or dimethoxyethane. It is also possible to use mixtures of the solvents mentioned. Acetonitrile is particularly preferred.

The process according to the invention is in general carried out in a temperature range from 0° C. to +180° C., preferably from +30° C. to +150° C.

The process steps according to the invention are in general carried out at normal pressure. However, it is also possible to work at elevated pressure or at reduced pressure (e.g. in a range from 0.5 to 5 bar).

The compound of the formula (VI) is known [cf. F. I. Logemann, G. Shaw, Chemistry and Industry, 1980 (13), 541–542].

The compounds of the general formulae (III) and (VII) are known per se or can be prepared according to customary methods.

The amines of the general formula (VIII) are known or can be prepared according to known methods [cf. L. R. Krepski et al., Synthesis, 1986, 301–303].

The compounds of the general formula (IV) are new and can be prepared as described above.

The compounds of the general formula (I) according to the invention show an unforeseeable, useful spectrum of pharmacological action.

They inhibit either one or more of the c-GMP-metabolizing phosphodiesterases (PDE I, PDE II and PDE V). This leads to a differentiated c-GMP-rise. An increase in the c-GMP level can lead to an antithrombotic, vasodilatory and/or antiarrhythmic action. The differentiating action is additionally determined by the distribution of the isoenzymes in the tissue.

The compounds according to the invention additionally potentiate the action of substances, such as, for example, EDRF (endothelium-derived relaxing factor) and ANP (atrial natriuretic peptide) which raise the c-GMP level.

They can therefore be employed in medicaments for the treatment of cardiovascular disorders, such as, for example, for the treatment of high blood pressure, neuronal hypertension, stable and unstable angina, peripheral and cardiac vascular disorders, of arrhythmias, for the treatment of thromboembolic disorders and ischaemias such as myocardial infarct, cerebral infarct, transitory and ischaemic attacks, angina pectoris, peripheral circulatory disorders, prevention of restenoses after thrombolysis therapy, percutaneous transluminal angioplasty (PTA), percutaneous transluminal coronary angioplasty (PTCA) and bypass. The relaxing action on the smooth musculature makes them suitable for the treatment of disorders of the urogenital system such as prostate hypertrophy, impotence and incontinence. They can furthermore also have significance for cerebrovascular disorders.

Activity of the Phosphodiesterases (PDEs)

The c-GMP-stimulable PDE II, the c-GMP-inhibitable PDE III and the cAMP-specific PDE IV were isolated either from porcine or bovine myocardium. The $Ca^{2+}$ calmodulin-stimulable PDE I was isolated from porcine aorta, porcine brain or preferably from bovine aorta The c-GMP-specific PDE V was obtained from porcine small intestine, porcine aorta, human blood platelets and preferably from bovine aorta. Purification was carried out by anion exchange chromatography on Mono® Pharmacia essentially according to the method of M. Hoey and Miles D. Houslay, Biochemical Pharmacology, Vol. 40, 193–202 (1990) and C. Lugman et al., Biochemical Pharmacology Vol. 35, 1743–1751 (1986).

The enzyme activity was determined in a test mixture of 100 μl in 20 mM tris/HCl buffer ph 7.5 which contains 5 MM $MgCl_2$, 0.1 mg/ml of bovine serum albumin and either 800 Bq of $^3$HcAMP or $^3$HcGMP. The final concentration of the corresponding nucleotides is $10^{-6}$ mol/l. The reaction is started by addition of the enzyme; the amount of enzyme is proportioned such that during the incubation time of 30 min about 50% of the substrate is reacted. In order to test the cGMP-stimulable PDE II, $^3$HcAMP is used as a substrate and $10^{-6}$ mol/l of unlabelled cGMP is added to the mixture. In order to test the Ca calmodulin-dependent PDE I, additionally $CaCl_2$, 1 μM and calmodulin, 0.1 μM are added to the reaction mixture. The reaction is stopped by addition of 100 μl of acetonitrile which contains 1 mM cAMP and 1 mM AMP. 100 μl of the reaction mixture are separated on an HPLC and the cleavage products are quantitatively determined "on-line" using a flow scintillation counter. The substance concentration is measured at which the reaction rate is decreased by 50%. Additionally, the "phosphodiesterase [3H] cAMP-SPA enzyme assay" and the "phosphodiesterase [$^3$H] cGMP-SPA enzyme assay" from Amersham Life Science were used for testing. The test was carried out according to the experimental protocol indicated by the manufacturer. For activity determination of the PDE2, the [$^3$H] cAMP SPA assay was used, $10^{-6}$M cGMP being added to the reaction mixture to activate the enzyme. For the measurement of PDE1, calmodulin, $10^{-7}$M and $CaCl_2$, 1 μM were added to the reaction mixture. The PDE5 was measured using the [$^3$H] cGMP SPA assay.

Inhibition of the phosphodiesterases in vitro

| Ex. No. | PDE I $IC_{50}$ [nM] | PDE II $IC_{50}$ [nM] | PDE V $IC_{50}$ [nM] |
| --- | --- | --- | --- |
| 1 | 500 | 200 | 300 |
| 33 | 3000 | 100 | 800 |
| 34 | ~500 | 20 | 500 |
| 69 | 3000 | 60 | 500 |
| 80 | 100 | 80 | 1000 |
| 82 | 100 | 20 | 500 |
| 83 | 300 | 20 | 500 |
| 84 | 100 | 20 | 1000 |

-continued

| Ex. No. | PDE I IC$_{50}$ [nM] | PDE II IC$_{50}$ [nM] | PDE V IC$_{50}$ [nM] |
|---|---|---|---|
| 100 | 1000 | 4 | 1000 |
| 121 | 500 | 3 | 1000 |
| 122 | 500 | 4 | 1000 |
| 138 | 500 | 1 | 500 |

The compounds were examined for antihypertensive activity in the anaesthetized pig.

The erection-inducing action was measured in the anaesthetized rabbit. (C. G. Stief et al., World Journal Urology 1990, pp. 233–236).

The substances were administered intraduodenally, rectally, orally, transdermally or intravenously in doses of 0.03 to 10 mg/kg directly into the corpus cavernosum.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of approximately 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, it being possible, for example, if water is used as a diluent optionally organic solvents to use as auxiliary solvents.

Administration is carried out in the customary manner, preferably orally, transdermally or parenterally, in particular perlingually or intravenously.

In general, it has proved advantageous in the case of intravenous administration to administer amounts of approximately 0.01 to 10 mg/kg, preferably approximately 0.1 to 10 mg/kg of body weight, to achieve effective results.

In spite of this, if appropriate it may sometimes be necessary to depart from the amounts mentioned, mainly depending on the body weight or the type of administration route, on individual behaviour towards the medicament, the manner of its formulation and the time or interval at which administration takes place. Thus in some cases it may be sufficient to manage with less than the abovementioned minimum amount, while in other cases the upper limit mentioned has to be exceeded. In the case of the administration of relatively large amounts, it may be advisable to divide these into several individual doses over the course of the day.

Starting Compounds

1.) The amines (formula VII/R$^2$=alkyl) are prepared from the corresponding substituted phenethyl halides by addition to the appropriate β-keto esters, hydrolysis and decarboxylation and reductive amination of the corresponding ketones with sodium cyanoborohydride [cf. Lane, Synthesis, 1975, 135–146].

2.) The hydroxyamines (formula VII/R$^2$=hydroxy-subst. alkyl) are prepared in a one-pot reaction from an aldehyde or ketone by addition of trimethylsilyl cyanide, reaction of the corresponding silylated cyanohydrins with Grignard reagents and reduction of the imines with sodium borohydride [cf. Krepski, Jensen, Heilmann, Rasmussen, Synthesis, 1986, 301–103].

3.) 1-Substituted 5-amino-imidazole-carboxamides (formula II)

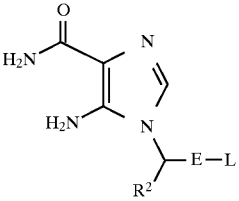

Synthesis from 2-anino-2-cyano-acetamide (I. I. Logemann and G. Shaw, Chem. Ind. (London) 541, 1980) and the appropriate amine (see 1.)) or hydroxyamine (see 2.)) according to P. R. Birkett, C. B. Chapler and G. Mackenzie, Synthesis 1991, 157–159 or G. Shaw, R. W. Warrener, N. D. Butler and R. K. Ralph, J. Chem. Soc., 1959, 1644–1655.

PREPARATION EXAMPLES

Preparation of the purin-6-ones

Method A:

22 mmol of 1-substituted-5-amino-imidazole-4-carboxamide are refluxed with 1.76 g (44 mmol) of sodium hydride (60% strength) in 300 ml of abs. THF for 30 minutes. After cooling to 0° C., 40 mmol of the appropriate acid chloride are added dropwise in 50 ml of abs. THF. The mixture is stirred overnight at room temperature and concentrated on a rotary evaporator after dropwise addition of 20 ml of methanol. The residue is purified by flash chromatography on silica gel (eluent: CH$_2$Cl$_2$/MeOH mixture) and the 5-acylamino-imidazole-4-carboxamides, which can be directly reacted further, are obtained.

10 mmol of the 5-acylamino-imidazole-4-carboxamide and 5.52 g (40 mmol) of K$_2$CO$_3$ are refluxed overnight in 100 ml of methanol and 30 ml of water. The mixture is acidified to pH 1 to 2 by addition of 2N hydrochloric acid. The methanol is stripped off in vacuo, 100 ml of water are added and the mixture is extracted twice by shaking with 100 ml of ethyl acetate each time. After drying the combined organic phases over Na$_2$SO$_4$, the mixture is concentrated on a rotary evaporator and the residue is purified by flash chromatography on silica gel (eluent: CH$_2$Cl$_2$/MeOH mixture). The fractions containing the product are combined and evaporated. Solid residues are recrystallized from ethyl acetate or ethyl acetate/diethyl ether.

Method B:

3.3 mmol of the corresponding acid chloride in a little abs. THF are added dropwise at room temperature to a solution of 3 mmol of the 1-substituted-5-amino-imidazole4-carboxamide and 50 mg of DMAP in 20 ml of abs. pyridine. After 30 minutes at room temperature, the mixture is stirred at 50° C. for about 5 more hours (TLC checking). The mixture is evaporated, the residue is taken up in 20 ml of CH$_2$Cl$_2$ and the solution is washed with 20 ml of 2N HCl. After drying the organic phase over Na$_2$SO$_4$, it is evaporated and the residue is purified by flash chromatography on silica gel (eluent: CH$_2$Cl$_2$/MeOH mixture). The 5-acylamino-imidazole4-carboxamides are obtained, which are directly reacted further as described in Method A.

Method C:

2 mmol of 1-substituted-5-amino-imidazole-4-carboxamide and 8 mmol of the appropriate ester are refluxed for 18 hours in 20 ml of a sodium ethoxide-ethanol solution (prepared from 0.23 g (10 mmol) of sodium and 20 ml of absolute ethanol). After cooling, the mixture is neutralized with glacial acetic acid and evaporated. The residue is purified by flash chromatography and the fractions containing the product are combined and evaporated. Solid residues are recrystallized from ethyl acetate or ethyl acetate/ether.

The purin-6-ones prepared according to Method A, B or C are compiled in Tables 1 and 2.

TABLE 1

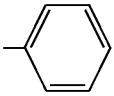

| Ex. No. | Z | D | R² | E | Yield (% of theory) | Mp.[1]/R$_f$[3] |
|---|---|---|---|---|---|---|
| 1 | 1 | 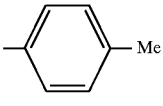 | Me | (CH$_2$)$_3$ | 63.5 | 135 |
| 2 | 1 | 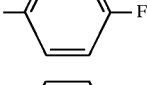 —Me | Me | (CH$_2$)$_3$ | 61 | 173 |
| 3 | 1 | 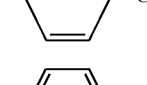 —F | Me | (CH$_2$)$_3$ | 58 | 164 |
| 4 | 1 |  —Cl | Me | (CH$_2$)$_3$ | 59 | 194 |
| 5 | 1 |  —NO$_2$ | Me | (CH$_2$)$_3$ | 41 | 151 |
| 6 | 1 | 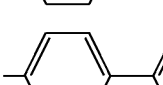 —Br | Me | (CH$_2$)$_3$ | 69 | 196 |
| 7 | 1 | 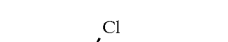 —OMe | Me | (CH$_2$)$_3$ | 61 | 0.54 |
| 8 | 1 | 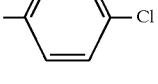 | Me | (CH$_2$)$_3$ | 31 | 152 |
| 9 | 1 | 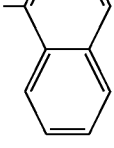 | Me | (CH$_2$)$_3$ | 19 | 107 |
| 10 | 1 |  | Me | (CH$_2$)$_3$ | 44 | 150 |

TABLE 1-continued
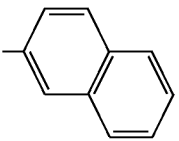
| Ex. No. | Z | D | R² | E | Yield (% of theory) | Mp.[1]/R_f[3] |
|---|---|---|---|---|---|---|
| 11 | 1 | 2-naphthyl | Me | (CH$_2$)$_3$ | 51 | 125 |
| 12[2] | 1 | 4-pyridyl | Me | (CH$_2$)$_3$ | 50 | 156 |
| 13[2] | 1 | 3-pyridyl | Me | (CH$_2$)$_3$ | 27 | 130 |
| 14 | 1 | 3-thienyl | Me | (CH$_2$)$_3$ | 81 | 171 |
| 15 | 2 | phenyl | Me | (CH$_2$)$_3$ | 68 | 187 |
| 16 | 2 | 4-MeO-phenyl | Me | (CH$_2$)$_3$ | 48 | 135 |
| 17 | 3 | phenyl | Me | (CH$_2$)$_3$ | 57 | 108 |
| 18 | 1 | phenyl | Iso-propyl | (CH$_2$)$_3$ | 56 | 154 |
| 19 | 1 | 4-Me-phenyl | Iso-Propyl | (CH$_2$)$_3$ | 50 | 0.46 |
| 20 | 1 | 3-Cl-phenyl | Me | (CH$_2$)$_3$ | 18.9 | 80 |
| 21 | 1 | 3-MeO-phenyl | Me | (CH$_2$)$_3$ | 50 | 122 |

TABLE 1-continued
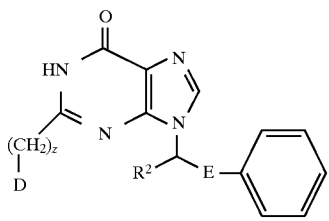
| Ex. No. | Z | D | R² | E | Yield (% of theory) | Mp.[1]/R_f[3] |
|---|---|---|---|---|---|---|
| 22 | 1 | 2-Cl-C₆H₄ | Me | (CH₂)₃ | 36 | 150 |
| 23 | 1 | 3,4-methylenedioxy-C₆H₃ | Me | (CH₂)₃ | 30.9 | 129 |
| 24 | 1 | 3,4-(OMe)₂-C₆H₃ | Me | (CH₂)₃ | 43.2 | 127 |
| 25 | 1 | 3-Me-C₆H₄ | Me | (CH₂)₃ | 29 | 0.55 |
| 26 | 1 | 2-Me-C₆H₄ | Me | (CH₂)₃ | 41.5 | 160 |
| 27 | 1 | 2,5-Me₂-C₆H₃ | Me | (CH₂)₃ | 43 | 160 |
| 28 | 1 | 3-OMe-C₆H₄ | Me | (CH₂)₃ | 77 | 0.52 |
| 29 | 1 | 2-F-C₆H₄ | Me | (CH₂)₃ | 22 | 0.45 |

TABLE 1-continued
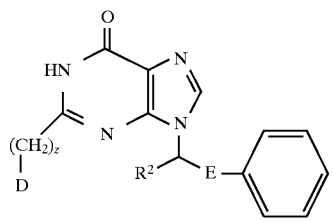
| Ex. No. | Z | D | R² | E | Yield (% of theory) | Mp.[1]/R_f[3] |
|---|---|---|---|---|---|---|
| 30 | 1 | 2,6-diCl-phenyl | Me | (CH₂)₃ | 36 | 157 |
| 31 | 1 | 2-CF₃-phenyl | Me | (CH₂)₃ | 60.7 | 200 |
| 32 | 1 | 3-CF₃-phenyl | Me | (CH₂)₃ | 31.4 | 126 |
[1] Crystallizes from ethyl acetate or ethyl acetate/ether
[2] Not acidified
[3] Eluent CH₂Cl₂/MeOH 10:1
TABLE 2
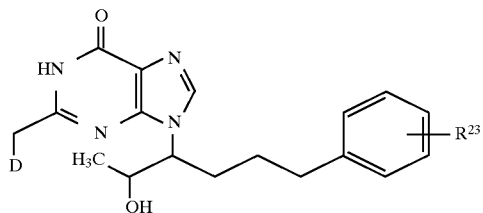
| Ex. No. | D | R[2] | Yield (% of theory) | Mp.[1]/R_f[2] |
|---|---|---|---|---|
| 33 | phenyl | H | 21 | 0.36 |
| 34 | 2,3-diCl-phenyl | H | 34 | 153 |
| 35 | 4-Cl-phenyl | H | 31 | 208 |

TABLE 2-continued
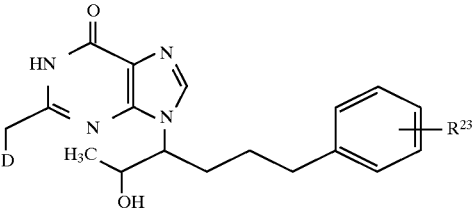
| Ex. No. | D | R[2] | Yield (% of theory) | Mp.[1]/R$_f$[2] |
|---|---|---|---|---|
| 36 | 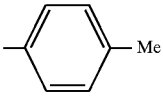 | 4-OMe | 56.1 | 202 |
| 37 | 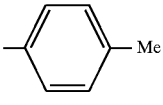 | 4-Me | 32 | 191 |
| 38 | 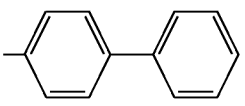 | 4-Me | 30 | 194 |
| 39 | 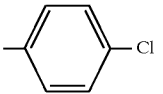 | 4-Me | 31.6 | 213 |
| 40 | 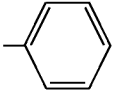 | 4-Me | 64.7 | 187 |
| 41 | 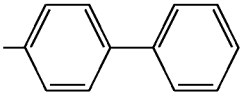 | 4-OMe | 41.6 | 184 |
| 42 | 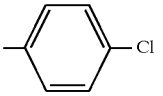 | 4-OMe | 39.5 | 212 |
| 43 | 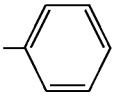 | 4-OMe | 39.6 | 161 |
| 44 | 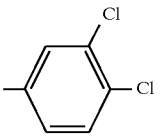 | 4-OMe | 36.5 | 164 |
| 45 | 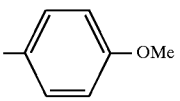 | 4-OMe | 31 | 187 |
| 46 | 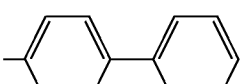 | H | 52.5 | 196 |
| 47 | 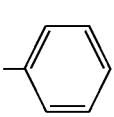 | 4-Cl | 52.3 | 200 |

TABLE 2-continued
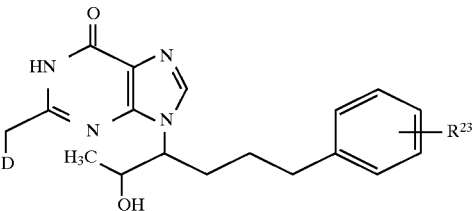
| Ex. No. | D | R[2)] | Yield (% of theory) | Mp.[1)]/R[f2)] |
|---|---|---|---|---|
| 48 | 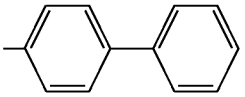 | 4-Cl | 55.3 | 199 |
| 49 | 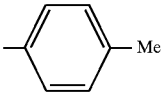 | 4-Cl | 53.2 | 207 |
| 50 | 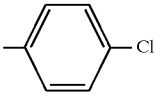 | 4-Cl | 49.7 | 209 |
| 51 | 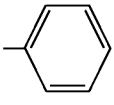 | 4-F | 38 | 168 |
| 52 | 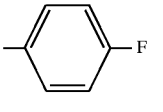 | 4-OMe | 38.6 | 179 |
| 53 | 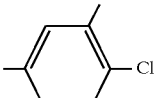 | 4-F | 20.2 | 175 |
| 54 | 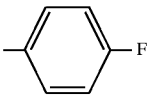 | H | 59.6 | 198 |
| 55 | 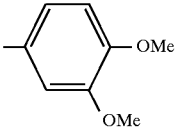 | H | 47.7 | 160 |
| 56 | 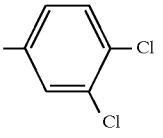 | 4-Me | 39.7 | 189 |
| 57 | 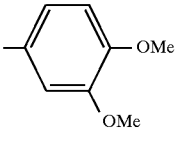 | 4-OMe | 60 | 196 |

TABLE 2-continued
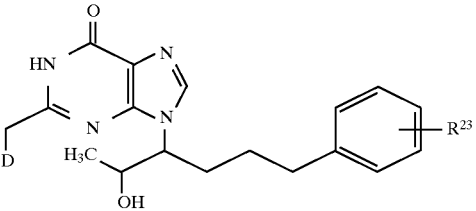
| Ex. No. | D | R[2)] | Yield (% of theory) | Mp.[1)]/R$_f$[2)] |
|---|---|---|---|---|
| 58 | 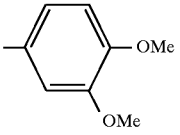 2,4-(OMe)$_2$-phenyl | 4-F | 60 | 183 |
| 59 | 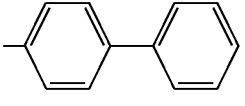 biphenyl | 4-F | 65.8 | 215 |
| 60 | 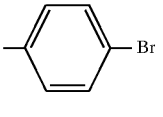 4-Br-phenyl | H | 40 | 225 |
| 61 | 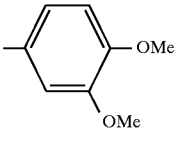 2,4-(OMe)$_2$-phenyl | 4-Cl | 52.3 | 150 |
| 62 | 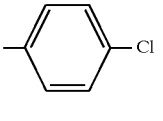 4-Cl-phenyl | 4-F | 93.4 | 210 |
| 63 | 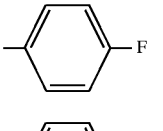 4-F-phenyl | 4-Cl | 33 | 188 |
| 64 | 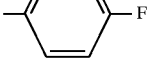 4-F-phenyl | 4-F | 47.4 | 165 |
| 65 | 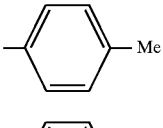 4-Me-phenyl | 4-F | 24.4 | 191 |
| 66[4)] | 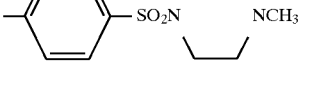 | H | 9 | 0.25 |
| 67 | 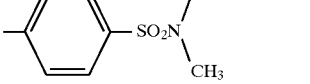 | H | 28.2 | 0.38 |
| 68 | 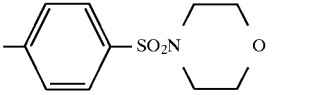 | H | 25.4 | 0.42 |

TABLE 2-continued

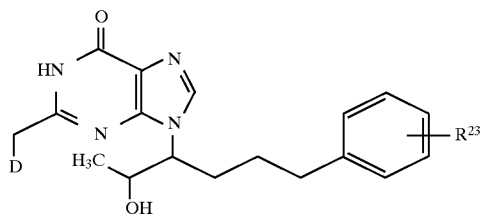

| Ex. No. | D | R[2)] | Yield (% of theory) | Mp.[1)]/R[f2)] |
|---|---|---|---|---|
| 69 | —C6H4—F (para) | H | 44.1 | 191 |
| 70[3)] | —C6H4—Me (para) (+ Enantiomer) | H | 27.5 | $[\alpha]_D^{20}$ = +14.0 (c = 1. DMSO) |
| 71[3)] | —C6H4—Me (para) (− Enantiomer) | H | 26 | $[\alpha]_D^{20}$ = −13.7 (c = 1. DMSO) |
| 72 | —C6H4—SO2NHCH3 | H | 23.9 | 0.29 |
| 73 | —C6H4—SO2NH—C(CH3)3 | H | 41 | 0.46 |
| 74 | —C6H4—SO2N(pyrrolidine) | H | 63.6 | 0.58 |
| 75 | —C6H4—SO2NH2 | H | 34.3 | 0.26 |
| 76[4)] | —C6H4—NH2 | H | 55 | 0.51 |
| 77[4)] | —C6H4—N(CH3)2 | H | 52.6 | 250 (dec.) |

[1)]Crystallizes from ethyl acetate or ethyl acetate/ether
[2)]Eluent CH2Cl2/MeOH 10:1
[3)]Resolution of enantiomers by column chromatography using a chiral support
[4)]Mixture concentrated on a rotary evaporator and residue purified directly by flash chromatography without extraction by shaking. R$_f$ determined using CH2Cl2/MeOH 10:1 + 1% NH3 as eluent

Example 78

9-(5-Phenyl-2-pentyl)-2-(4-p-methoxyphenylbenzyl)-purin-6-one

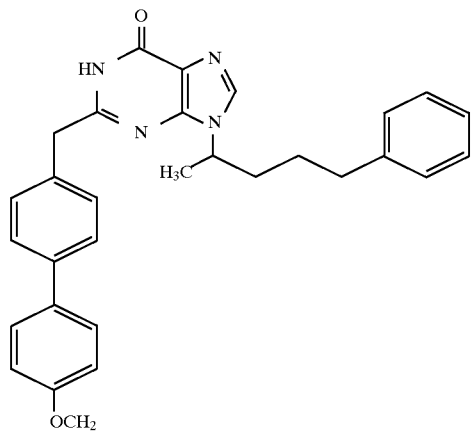

208 mg (0.46 mmol) of 9-(5-phenyl-2-pentyl)-2-(4-bromobenzyl)-purin-6-one (Example 6), 90 mg (0.59 mmol) of p-methoxyphenylboronic acid and 210 mg of bis(triphenylphosphine)-palladium(II) chloride are stirred at 70° C. for 1 h in 10 ml of abs. THF. 0.65 ml of 2N $Na_2CO_3$ solution are then added and the mixture is refluxed for 5 h (TLC checking). The mixture is evaporated and the residue is purified by flash chromatography (silica gel, eluent $CH_2Cl_2$/MeOH 30:1). The fractions containing the product are combined and evaporated. The residue is recrystallized from ethyl acetate/ether.

Yield: 161 mg (78.5%)

M.p.: 172° C.

The examples shown in Table 3 were prepared in an analogous manner:

TABLE 3

| Ex.-No. | $R^{24}$ | $R^2$ | Yield (% of theory) | Mp./$R_f$ |
|---|---|---|---|---|
| 79 | 4-Cl-phenyl | $CH_3$ | 27 | 170[1] |
| 80 | 4-F-phenyl | $CH_3$ | 69 | 193[2] |
| 81 | 3-$NO_2$-phenyl | $CH_3$ | 68 | 128[1] |
| 82 | 3-$NH_2$-phenyl | $CH_3$ | 54 | 178[1] |
| 83 | 3-thienyl | $CH_3$ | 79 | 199[1] |
| 84[4] | 3-pyridyl | $CH_3$ | 67 | 0.33[3] |
| 85[4] | 3-pyridyl | MeCH(OH) | 41.8 | 191 |
| 86 | 3-thienyl | MeCH(OH) | 49.6 | 209 |
| 87 | 4-OMe-phenyl | MeCH(OH) | 76.8 | 200 |
| 88 | 3-$NO_2$-phenyl | MeCH(OH) | 35.6 | 185 |
| 89 | 4-Cl-phenyl | MeCH(OH) | 43 | 182 |
| 90 | 4-F-phenyl | MeCH(OH) | 46 | 183 |

TABLE 3-continued

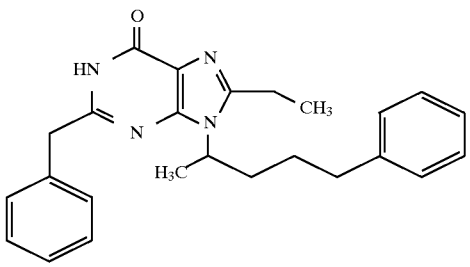

| Ex.-No. | R²⁴ | R² | Yield (% of theory) | Mp./R_f |
|---|---|---|---|---|
| 91 | (3-aminophenyl-methyl) | Me-CH(OH)- | 8 | 0.45³⁾ |
| 92 | (pyrimidinyl-methyl) | Me-CH(OH)- | 41.6 | 200 |

¹⁾Crystallizes from ethyl acetate/ether
²⁾Crystallizes from ether
³⁾Eluent $CH_2Cl_2$/MeOH 10:1
⁴⁾From (3-pyridyl-B(Et)₂) using Pd(PPh₃)₄ as catalyst

Example 93

9-(5-Phenyl-2-pentyl)-8-ethyl-2-benzyl-purin-6-one

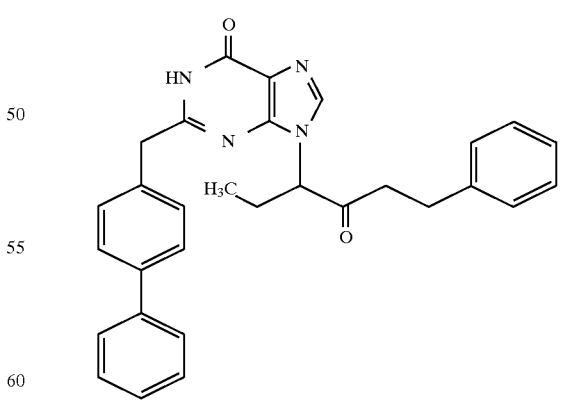

1.2 g (4 mmol) of 1-(5-phenyl-3-pentyl)-2-ethyl-5-aminoimidazole4-carboxamide are stirred at 50° C. for 30 minutes with 240 mg (6 mmol) of sodium hydride (60%) in 30 ml of abs. THF and 10 ml of abs. DMF. After cooling to 20° C., 773 mg (5 mmol) of phenylacetyl chloride in 10 ml of abs. THF are added dropwise and the mixture is stirred overnight at 20° C. 10 ml of $H_2O$, then 10 ml of 2N HCl, then 100 ml of ethyl acetate are slowly added. The organic phase is separated off, dried over $Na_2SO_4$ and evaporated. The residue is purified by flash chromatography (silica gel, eluent $CH_2Cl_2$/MeOH 50:1>20:1).

$R_f$=0.32 ($CH_2Cl_2$/MeOH 10:1)

Yield: 441 mg (26.4%)

440 mg (1.05 mmol) of the acylated imidazole-carboxamide and 0.58 g (4.2 mmol) of potassium carbonate are refluxed overnight in 20 ml of methanol and 5 ml of $H_2O$. After cooling, 10 ml of 2N HCl are added, the mixture is extracted twice by shaking with 20 ml of ethyl acetate each time and the combined ethyl acetate phases are washed once with water and once with satd. NaCl solution. After drying over $Na_2SO_4$, the organic phase is evaporated and the residue is purified by flash chromatography (silica gel, eluent $CH_2Cl_2$/MeOH 30:1>20:1).

Yield: 161 mg (38.3%)

$R_f$=0.33 ($CH_2Cl_2$/MeOH 10:1)

The examples shown in Table 4 are prepared in an analogous manner:

TABLE 4

[Structure of purine compound with D substituent]

| Ex.-No. | D | Yield (% of theory) | Mp./R_f¹⁾ |
|---|---|---|---|
| 94 | (4-methylphenyl)-CH₂- | 59 | 0.35 |
| 95 | (4-methoxyphenyl)-CH₂- | 39 | 0.32 |
| 96²⁾ | (3-pyridyl)-CH₂- | 64 | 0.26 |

¹⁾Eluent: $CH_2Cl_2$/MeOH 10:1
²⁾Not extracted by shaking with HCl

Example 97

9-(6-Phenyl-2-oxo-3-hexyl)-2-(4-phenyl-benzyl)-purin-6-one

[Structure]

478 mg (1 mmol) of 9-(6-phenyl-2-hydroxy-3-hexyl)-2-(4-phenyl-benzyl)-purin-6-one (Ex. 46) and 1.3 ml of triethylamine are dissolved in 10 ml of $CH_2Cl_2$ and 3 ml of DMSO and 0.7 g of pyridine/$SO_3$ complex is added at 0° C. The mixture is stirred at 20° C. for 16 h and extracted by shaking with 10 ml of 2N HCl and 10 ml of saturated NaHCO₃ solution once each. After drying the organic phase over Na₂SO₄, it is evaporated and the residue is purified by flash chromatography on silica gel (eluent: CH₂Cl₂/MeOH 40:1). Yield: 425 mg (89.3%), $R_f$=0.52 (CH₂Cl₂/MeOH 30:1)

The compounds shown in Table 5 are prepared in an analogous manner.

TABLE 5

| Ex. No. | D | R²⁵ | Yield | $R_f^{1)}$ |
|---|---|---|---|---|
| 98 | 4-Me-phenyl | 4-OMe | 41.9 | 0.63 |
| 99 | 4-F-phenyl | H | 76.6 | 0.59 |
| 100 | 3,4-di-OMe-phenyl | H | 50 | 0.56 |
| 101 | 4-Br-phenyl | H | 38.2 | 0.55 |
| 102 | 3,4-di-OMe-phenyl | 4-OMe | 40 | 0.55 |
| 103 | 3,4-di-OMe-phenyl | 4-F | 35 | 0.54 |
| 104 | 3,4-di-OMe-phenyl | 4-Cl | 11.5 | 0.49 |
| 105 | 4-Br-phenyl | H | 62.8 | 0.54 |
| 106 | biphenyl | 4-F | 25 | 0.48 |

¹⁾Eluent: CH₂Cl₂/MeOH 30:1

Example 107

9-(5-Phenyl-2-pentyl)-2-(4-hydroxybenzyl)-purin-6-one

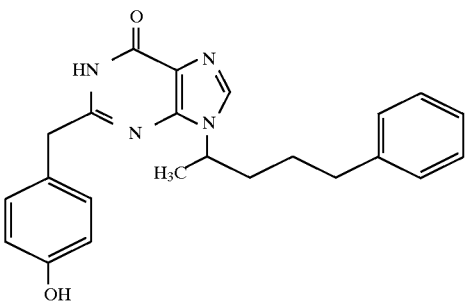

2.2 ml of a 1 molar solution of boron tribromide in CH₂Cl₂ are added dropwise at −78° C. to 404 mg (1 mmol) of the compound from Example 7 in 5 ml of abs. CH₂Cl₂. After 30 minutes at −78° C., the mixture is stirred at 20° C. for 2 hours. As starting substance was still to be seen in the thin-layer chromatogram, a further 1.1 ml of the 1 molar BBr₃ solution were added dropwise at −78° C. After stirring overnight at room temperature, the mixture is cooled to −78° C., and 5 ml of methanol are added dropwise. The mixture is evaporated, the residue is taken up in 10 ml of CH₂Cl₂ and the solution is extracted twice by shaking with 10 ml of 10% NaOH solution each time. The combined NaOH phases are acidified to pH 1–2 by addition of conc. HCl solution and extracted twice by shaking with 30 ml of ethyl acetate each time. The combined ethyl acetate phases are evaporated and the residue is purified by flash chromatography (silica gel, eluent CH₂Cl₂/MeOH 50:1→30:1). Recrystallization from ethyl acetate/ether.

Yield: 250 mg (64.4%)

M.p.: 184° C.

Example 108

9-(1-Benzyloxy-2-propyl)-2-benzyl-purin-6-one

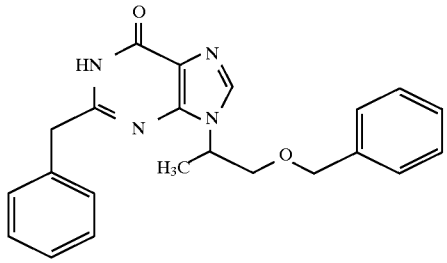

a) 22 g (0.22 mol) of 2-amino-2-cyano-acetamide and 37 ml of triethyl orthoformate are refluxed in 200 ml of acetonitrile for 1 hour. 17.5 ml of 2-amino-1-propanol are then added and the mixture is refluxed for a further 15 minutes. After cooling, it is concentrated, and the residue is dissolved in a little methanol and purified by flash chromatography on silica gel (eluent CH₂Cl₂/MeOH 10:1). The yield of crystalline 5-amino-1-(1-hydroxy-2-propyl)-imidazole-4-carboxamide is 24.3 g (60%).

b) 24 g (0.13 mol) of the compound from step a) are stirred at 50° C. for 2 hours with 25 ml of acetic anhydride and 30 ml of pyridine in 100 ml of abs. CH₂Cl₂. After cooling, the mixture is extracted by shaking with std. NaCl, and the organic phase is dried over $Na_2SO_4$ and evaporated. The residue is crystallized from ethyl acetate/ether. The yield of 5-amino-1-(1-acetoxy-2-propyl)-imidazole-4-carboxamide is 23.4 g (84.2%).

c) 23 g (0.107 mol) of the compound from step b) and 1 g of DMAP (dimethylaminopyridine) are dissolved in 100 ml of pyridine. A solution of 12.1 ml of phenylacetyl chloride in 20 ml of abs. toluene is added dropwise to this solution and it is stirred at 20° C. for 30 minutes. It is then stirred at 60° C. for 2 hours and evaporated, the residue is added to 100 ml of abs. toluene and the mixture is evaporated again. The residue is dissolved in methylene chloride and the organic phase is washed with water. The product crystallizes out of the methylene chloride phase, and is filtered off with suction, dried and directly reacted further without further purification. The yield of 5-phenylacetylamino-1-(1-acetoxy-2-propyl)-imidazole-4-carboxamide is 12.8 g (36%).

d) 12.8 g (38.5 mmol) of the compound from step c) and 6.2 g (155 mmol) of NaOH are refluxed for 3 hours in 100 ml of a methanol/water mixture (1:1). After cooling, the mixture is acidified with 10% HCl and extracted twice with ethyl acetate. The combined ethyl acetate phases are washed with saturated NaCl solution, dried over $Na_2SO_4$ and evaporated. The residue is recrystallized from ethyl acetate/ether. The yield of 9-(1-hydroxy-2-propyl)-2-benzylpurin-6-one is 6.2 g (55.2%), M.p.: 192° C.

e) 576 mg (2 mmol) of the purin-6-one from step d) and 200 mg of NaH (60% strength) are refluxed for 30 minutes in 30 ml of abs. THF. After cooling, 0.3 ml (2.4 mmol) of benzyl chloride are added dropwise in a little abs. THF at 20° C. and the mixture is stirred for 16 hours. 5 ml of $H_2O$ are added dropwise, then the mixture is evaporated and the residue is taken up in ethyl acetate. The organic phase is washed with 2N HCl and saturated NaCl solution, dried over $Na_2SO_4$ and evaporated. The residue is purified by flash chromatography on silica gel (eluent: $CH_2Cl_2$/MeOH 40:1). The fractions containing the product are combined and evaporated. The residue is crystallized using diethyl ether. Yield 510 mg (67.5%), M.p. 149° C.

Example 109

9-(1-p-Chlorobenzyloxy-2-propyl)-2-benzyl-purin-6-one

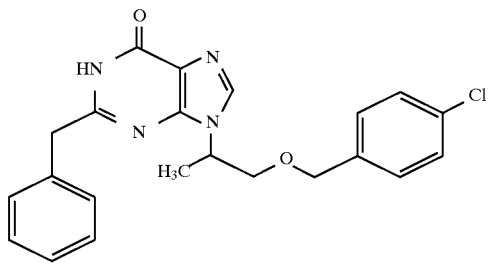

The title compound was prepared in an analogous manner to the procedure of Example 108. Yield: 59%, m.p. 166° C.

The examples shown in Table 6 were prepared according to the procedures mentioned above in analogy to the compounds from Table 2, as a rule according to method c).

TABLE 6

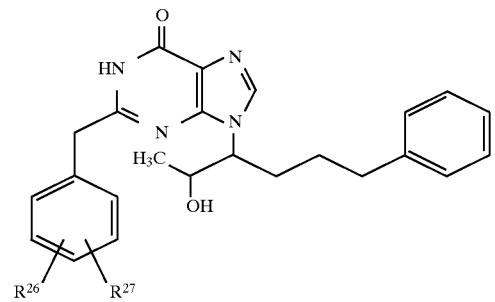

| Ex. No. | $R^{26}/R^{27}$ | Yield (% of theory) | Mp C./$R_f$ |
|---|---|---|---|
| 110 | 4-NH—$COCH_3$/H | 44 | 236[1] |
| 111 | 4-$NHSO_2CH_3$/H | 60.6 | 0.28[3] |
| 112 | 4-NH—$COCH_2OCH_3$/H | 34 | 201[1] |
| 113 | 4-$SO_2$N(piperidine-$CO_2C_2H_5$)/H | 46.2 | 0.5[3] |
| 114 | 4-$SO_2NH$—$CH_2CH_2$—N($CH_3$)($CH_3$)/H | 31 | 0.16[4] |
| 115 | 4-NH—CO—$CH_2CH_2$—N($CH_3$)($CH_3$)/H | 59 | 0.46[5] |
| 116 | 4-$SO_2NH$—$CH_2CH_2$—OH/H | 15.2 | 0.29[3] |

TABLE 6-continued

| Ex. No. | $R^{26}/R^{27}$ | Yield (% of theory) | Mp C./$R_f$ |
|---|---|---|---|
| 117 | 4-SO$_2$NH-CH$_2$CH$_2$-OCH$_3$/H | 19.8 | 0.48[3)] |
| 118 | 4-SO$_2$N(piperidine-4-CO$_2$H[6)])/H | 64.5 | 0.32[4)] |
| 119 | 4-NH—CONH$_2$/H | 89 | 0.27[4)] |
| 120 | 4-NH—CHO/H | 28 | 0.37[5)] |
| 121 | 4-NH—CO-(piperidine-N—CO$_2$—CH$_2$—C$_6$H$_5$)/H | 13.2 | 0.46[5)] |
| 122 | 4-NH—CO-(piperidine-N—CO$_2$C$_2$H$_5$)/H | 36.5 | 0.4[5)] |
| 123 | 4-NH—CO—NHCH$_3$/H | 67.3 | 225[1)] |
| 124 | 4-SO$_2$NH—COCH$_3$/H | 25.5 | 0.38[4)] |
| 125 | 4-NH—CO—N(CH$_3$)$_2$ | 12.2 | 0.39[5)] |
| 126 | 4-SO$_2$NH—CO$_2$CH$_3$/H | 6.2 | 0.25[4)] |
| 127 | 4-O-CH$_2$-CH=CH$_2$/H | 78.6 | 174[1)] |
| 128 | 4-O-CH$_2$-CH(OH)-CH$_2$-OH/H | 55.5 | 0.25[4)] |
| 129 | 3-SO$_2$—N(piperazine-N—CH$_3$)/4-OCH$_3$ | 25.2 | 0.3[3)] |
| 130 | 4-SO$_2$NH—CONHCH$_3$ | 17.4 | 0.39[4)] |
| 131 | 4-O—CH$_2$—CO$_2$CH$_3$ | 47.9 | 146[1)] |
| 132 | 4-O—CH$_2$—CO$_2$H[7)] | 93 | 0.37[3)] |
| 133 | 3-SO$_2$NH-CH$_2$CH$_2$-N(CH$_3$)$_2$/4-OCH$_3$ | 40.9 | 0.23[4)] |
| 134 | 3-SO$_2$NH-CH$_2$CH$_2$-OCH$_3$/4-OCH$_3$ | 37.6 | 0.29[3)] |
| 135 | 3-SO$_2$NH-CH$_2$CH$_2$-OH/4-OCH$_3$ | 44.9 | 0.14[3)] |
| 136 | 3-SO$_2$NHCH$_3$/4-OCH$_3$ | 56.5 | 0.23[3)] |

TABLE 6-continued

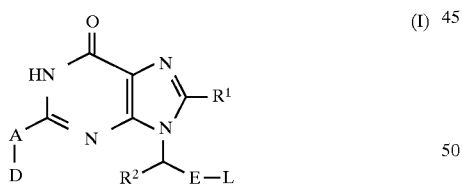

| Ex. No. | $R^{26}/R^{27}$ | Yield (% of theory) | Mp C./$R_f$ |
|---|---|---|---|
| 137 | 3-SO$_2$N(piperidine)-CO$_2$C$_2$H$_5$/4-OCH$_3$ | 61 | 0.37[3] |
| 138 | 3-SO$_2$N(piperidine)-CO$_2$H[8]/4-OCH$_3$ | 54 | 0.16[3] |
| 139 | 3-NO$_2$/4-OH | 56.5 | 146° C.[1] |
| 140 | 3-NO$_2$/4-OC$_2$H$_5$ | 57 | 180° C.[1] |
| 141 | 3-NH$_2$/4-OCH$_3$ | 58 | 187° C.[1] (dec.) |
| 142 | 3-NH$_2$/4-OH | 31.5 | 152° C.[1] (dec.) |
| 143 | 3-NHSO$_2$CH$_3$/4-OCH$_3$ | 63 | 132° C.[1] |
| 144 | 3-NH—COCH$_3$/4-OCH$_3$ | 54.5 | 0.42[3] |
| 145 | 3-NH—COCH$_3$/4-OH | 33.6 | 0.45[3] |

[1] Crystallizes from ethyl acetate/ether
[2] Crystallizes from ether
[3] Eluent: CH$_2$Cl$_2$/CH$_3$OH 10:1
[4] Eluent: CH$_2$Cl$_2$/CH$_3$OH 7:1
[5] Eluent: CH$_2$Cl$_2$/MeOH 10:1 + 1% NH$_3$
[6] Prepared by hydrolysis of the corresponding ester Example 113
[7] Prepared by hydrolysis of the corresponding ester Example 131
[8] Prepared by hydrolysis of the corresponding ester Example 137

We claim:

1. Purin-6-one derivative of the formula (I)

$$\text{(I)}$$

in which
- $R^1$ represents hydrogen or straight-chain or branched alkyl having up to 8 carbon atoms,
- $R^2$ represents straight-chain or branched alkanoyl having up to 4 carbon atoms, or represents straight-chain or branched alkyl having up to 8 carbon atoms, which is optionally substituted by hydroxyl, azido or by a group of the formula —$NR^3R^4$ or —$OSO_2R^5$,
  in which
  - $R^3$ and $R^4$ are identical and different and denote cycloalkyl having 3 to 6 carbon atoms, hydrogen, formyl or straight-chain or branched alkyl having up to 6 carbon atoms, which is optionally substituted by hydroxyl, carboxyl or by straight-chain or branched alkoxy or alkoxycarbonyl each having up to 6 carbon atoms or by a group of the formula —(CO)$_a$—$NR^6R^7$, in which
  - a denotes a number 0 or 1,
  - $R^6$ and $R^7$ are identical or different and denote hydrogen, formyl, hydroxyl, phenyl or straight-chain or branched alkyl having up to 6 carbon atoms, which is optionally substituted by hydroxyl or by straight-chain or branched alkoxy having up to 5 carbon atoms,
  or
  - $R^3$ and/or $R^4$ denote straight-chain or branched alkoxycarbonyl having up to 6 carbon atoms, or carboxyl,
  or
  - $R^3$ and/or $R^4$ denote a radical of the formula —(CO)$_b$—T—$NR^8R^9$, —CO—$R^{10}$, —$SO_2R^{11}$ or —$SO_2NR^{12}R^{13}$, in which
    - b denotes the number 1,
    - T denotes straight-chain or branched alkyl having up to 5 carbon atoms,
    - or T can also denote a bond,
    - $R^8$ and $R^9$ have the meaning of $R^6$ and $R^7$ indicated above and are identical to or different from this,
    - $R^{10}$ denotes a saturated, partially unsaturated or unsaturated 5- to 7-membered heterocycle having up to 3 heteroatoms selected from the group consisting of S, N and O, which can optionally be substituted by straight-chain or branched alkyl, alkoxy or alkoxycarbonyl each having up to 4 carbon atoms, carboxyl, benzyloxycarbonyl or hydroxyl, $R^{11}$ denotes straight-chain or branched alkyl having up to 5 carbon atoms, benzyl or phenyl, $R^{12}$ and $R^{13}$ are identical or different and denote hydrogen, phenyl or straight-chain or branched alkyl having up to 6 carbon atoms, or $R^3$ and $R^4$, together with the nitrogen atom, form a 5- or 6-membered saturated, partially unsaturated or unsaturated heterocycle which can contain up to 3 heteroatoms selected from the group consisting of N, S and O or a radical —$NR^{14}$, and which is optionally substituted by carboxyl, by straight-chain or branched alkoxycarbonyl having up to 5 carbon atoms or by straight-chain or branched alkyl having up to 5 carbon atoms, which can be substituted by hydroxyl, carboxyl or by straight-chain or branched alkoxy or alkoxycarbonyl each having up to 6 carbon atoms, in which $R^{14}$ denotes hydrogen, or straight-chain or branched alkyl or alkoxycarbonyl each having up to 5 carbon atoms, and $R^5$ denotes phenyl or straight-chain or branched alkyl having up to 5 carbon atoms A represents a straight-chain or branched alkylene or alkenylene chain each having up to 6 carbon atoms, D and L are identical or different and represent aryl having 6 to 10 carbon atoms or a 5- to 7-membered aromatic, optionally benzo-fused heterocycle having up to 3 heteroatoms selected from the group consisting of S, N and O, each of said aryl or heterocycle being optionally substituted up to 3 times identically or differently by halogen, hydroxyl, nitro, trifluoromethyl, carboxyl, straight-chain or branched alkyl, alkoxy or alkoxycarbonyl each having up to 6 carbon atoms or by a group of the formula —$(V_c)$—$NR^{15}R^{16}$ and/or —$OR^{17}$, in which c denotes a number 0 or 1, V denotes a radical of the formula —CO or —$SO_2$, $R^{15}$ and $R^{16}$ are identical or different and have the meaning of $R^3$ and $R^4$ indicated above, $R^{17}$ denotes hydrogen, straight-chain or branched alkenyl having up to 8 carbon atoms or straight-chain or branched alkyl having up to 8 carbon atoms, which is optionally substituted up to 3 times identically or differently by hydroxyl, carboxyl or straight-chain or branched alkoxycarbonyl having up to 5 carbon atoms, and/or said aryl or heterocycle D or L is optionally substituted by aryl having 6 to 10 carbon atoms or by a 5- to 7-membered aromatic, optionally benzo-fused heterocycle having up to 3 heteroatoms selected from the group consisting of S, N and O, each of which aryl or heterocycle substituent on D or L is optionally substituted up to 2 times identically or differently by halogen, hydroxyl, nitro, carboxyl, trifluoromethyl or by straight-chain or branched alkyl, alkoxy or alkoxycarbonyl each having up to 5 carbon atoms or by a group of the formula($V'_d$)—$NR^{18}R^{19}$, in which d has the meaning of a indicated above and is identical to or different from this, $R^{18}$ and $R^{19}$ have the meaning of $R^3$ and $R^4$ indicated above and are identical to or different from this, V' has the meaning of V indicated above and is identical to or different from this, or D represents a radical of the formula

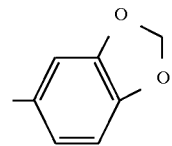

and

E represents a radical of the formula —$CH_2$—Y—Z—, in which

Y denotes a bond or an oxygen or sulphur atom or the —NH group,

Z denotes a straight-chain or branched alkylene chain having up to 5 carbon atoms, or a tautomer or a salt thereof.

2. Purin-6-one derivative of the formula (I) according to claim 1, in which $R^1$ represents hydrogen or straight-chain or branched alkyl having up to 6 carbon atoms, $R^2$ represents straight-chain or branched alkanoyl having up to 4 carbon atoms, or represents straight-chain or branched alkyl having up to 6 carbon atoms, which is optionally substituted by hydroxyl, azido or by a group of the formula —$NR^3R^4$ or O—$SO_2$—$R^5$, in which $R^3$ and $R^4$ are identical and different and denote cyclopentyl, cyclohexyl, hydrogen, formyl or straight-chain or branched alkyl having up to 5 carbon atoms, which is optionally substituted by hydroxyl, carboxyl or by straight-chain or branched alkoxy or alkoxycarbonyl each having up to 5 carbon atoms or by a group of the formula —$(CO)_a$—$NR^6R^7$, in which a denotes the number 0 or 1, $R^6$ and $R^7$ are identical or different and denote hydrogen, formyl, hydroxyl, phenyl or straight-chain or branched alkyl having up to 5 carbon atoms, which is optionally substituted by hydroxyl or by straight-chain or branched alkoxy having up to 4 carbon atoms, or $R^3$ and/or $R^4$ denote straight-chain or branched alkoxycarbonyl having up to 5 carbon atoms, or carboxyl, or $R^3$ and/or $R^4$ denote a radical of the formula —$(CO)_b$—T—$NR^8R^9$, —CO—$R^{10}$, —$SO_2R^{11}$ or —$SO_2NR^{12}R^{13}$, in which b denotes the number 1, T denotes straight-chain or branched alkyl having up to 4 carbon atoms, or T can also denote a bond, $R^8$ and $R^9$ have the meaning of $R^6$ and $R^7$ indicated above and are identical to or different from this, $R^{10}$ denotes morpholino, imidazolyl, pyridyl, piperazinyl, piperidinyl or pyrrolidinyl, each of which can optionally be substituted by straight-chain or branched alkyl, alkoxy or alkoxycarbonyl each having up to 3 carbon atoms, carboxyl, benzyloxycarbonyl or hydroxyl, $R^{11}$ denotes straight-chain or branched alkyl having up to 4 carbon atoms, benzyl or phenyl, $R^{12}$ and $R^{13}$ are identical or different and denote hydrogen, phenyl or straight-chain or branched alkyl having up to 5 carbon atoms, or $R^3$ and $R^4$, together with the nitrogen atom, form a pyrrolidinyl, morpholinyl, imidazolyl, piperidinyl or piperazinyl ring, each of which optionally can be substituted by straight-chain or branched alkoxycarbonyl having up to 4 carbon atoms, carboxyl, or by straight-chain or branched alkyl having up to 4 carbon atoms, which can be substituted by carboxyl, hydroxyl or by straight-chain or branched alkoxy or alkoxycarbonyl each having up to 4 carbon atoms, and $R^5$ denotes phenyl or straight-chain or branched alkyl having up to 4 carbon atoms A represents a straight-chain or branched alkylene or alkenylene chain each having up to 5 carbon atoms, D and L are identical or different and represent phenyl, naphthyl, pyridyl, pyrimidyl, thienyl, indolyl or furyl, each of which is optionally substituted up to 3 times identically or differently by fluorine, chlorine, bromine, trifluoromethyl, nitro, carboxyl, straight-chain or branched alkyl or alkoxycarbonyl each having up to 5 carbon atoms or by a group of the formula —$(V_c)$—$NR^{15}R^{16}$ and/or —$OR^{17}$, in which c denotes a number 0 or 1, V denotes a radical of the formula —CO or —$SO_2$, $R^{15}$ and $R^{16}$ are identical or different and have the meaning of $R^3$ and $R^4$ indicated above, $R^{17}$ denotes hydrogen, straight-chain or branched alkenyl having up to 6 carbon atoms or straight-chain or branched alkyl having up to 6 carbon atoms, which is optionally substituted up to 2 times identically or differently by hydroxyl, carboxyl or straight-chain or branched alkoxycarbonyl having up to 4 carbon atoms, and/or said aryl or heterocycle D or L is optionally substituted by naphthyl, phenyl, pyridyl, indolyl, thienyl, furyl, pyridazinyl, pyridyl, pyrryl or pyrimidyl, each of which is optionally substituted by fluorine, chlorine, bromine, hydroxyl, nitro, carboxyl, trifluoromethyl or by straight-chain or branched alkyl, alkoxy or alkoxycarbonyl each having up to 3 carbon atoms or by a group of the formula$(V'_d)$—$NR^{18}R^{19}$, in which d has the meaning of a indicated above and is identical to or different from this, V' has the meaning of V indicated above and is identical to or different from this, $R^{18}$ and $R^{19}$ have the meaning of $R^3$ and $R^4$ indicated above, or D represents a radical of the formula

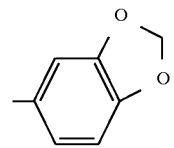

and

E represents a radical of the formula —$CH_2$—Y—Z—, in which

Y denotes a bond or an oxygen or sulphur atom or the —NH group,

Z denotes a straight-chain or branched alkylene chain having up to 4 carbon atoms, or a tautomer or a salt thereof.

3. Purin-6-one derivative of the formula (I) according to claim 1, in which $R^1$ represents hydrogen or straight-chain or branched alkyl having up to 4 carbon atoms, $R^2$ represents straight-chain or branched alkanoyl having up to 4 carbon atoms, or represents straight-chain or branched alkyl having up to 5 carbon atoms, which is optionally substituted by hydroxyl, azido or by a group of the formula —$NR^3R^4$ or O—$SO_2R^5$, in which $R^3$ and $R^4$ are identical and different and denote cyclopentyl, hydrogen, formyl or straight-chain or branched alkyl having up to 4 carbon atoms, which is optionally substituted by hydroxyl, carboxyl or by straight-chain or branched alkoxy or alkoxycarbonyl each having up to 3 carbon atoms or by a group of the formula —$(CO)_a$—$NR^6R^7$, in which a denotes a number 0 or 1, $R^6$ and $R^7$ are identical or different and denote hydrogen, formyl, hydroxyl, or straight-chain or branched alkyl having up to 3 carbon atoms, which is optionally substituted by hydroxyl or by straight-chain or branched alkoxy having up to 3 carbon atoms, or $R^3$ and/or $R^4$ denote straight-chain or branched alkoxycarbonyl having up to 3 carbon atoms, or carboxyl, or $R^3$ and/or $R^4$ denote a radical of the formula —$(CO)_b$—T—$NR^8R^9$, —CO—$R^{10}$, —$SO_2R^{11}$ or —$SO_2NR^{12}R^{13}$, in which b denotes the number 1, T denotes straight-chain or branched alkyl having up to 3 carbon atoms, or T can also denote a bond, $R^8$ and $R^9$ have the meaning of $R^6$ and $R^7$ indicated above and are identical to or different from this, $R^{10}$ denotes morpholino, piperidinyl, piperazinyl or pyrrolidinyl, each of which can optionally be substituted by straight-chain or branched alkyl, alkoxy or alkoxycarbonyl each having up to 3 carbon atoms, benzyloxycarbonyl, carboxyl or hydroxyl, $R^{11}$ denotes straight-chain or branched alkyl having up to 3 carbon atoms, benzyl or phenyl, $R^{12}$ and $R^{13}$ are identical or different and denote hydrogen or straight-chain or branched alkyl having up to 4 carbon atoms, or $R^3$ and $R^4$, together with the nitrogen atom, form a pyrrolidinyl, morpholinyl, imidazolyl, piperidinyl or piperazinyl ring, each of which optionally can be substituted by straight-chain or branched alkoxycarbonyl each having up to 3 carbon atoms or carboxyl or by straight-chain or branched alkyl having up to 3 carbon atoms, which can be substituted by carboxyl, hydroxyl or by straight-chain or branched alkoxy or alkoxycarbonyl each having up to 3 carbon atoms, and $R^5$ denotes phenyl or straight-chain or branched alkyl having up to 3 carbon atoms A represents an ethenylene (-vinylene) or an alkylene chain having up to 4 carbon atoms, in which D and L are identical or different and represent phenyl, naphthyl, furyl, thienyl, indolyl or pyridyl, each of which is optionally substituted up to 2 times identically or differently by fluorine, chlorine, bromine, nitro, carboxyl, trifluoromethyl, straight-chain or branched alkyl or alkoxycarbonyl each having up to 4 carbon atoms or by a group of the formula —($V_c$)—$NR^{15}R^{16}$ and/or —$OR^{17}$, in which c denotes a number 0 or 1, V denotes a radical of the formula —CO or —$SO_2$, $R^{15}$ and $R^{16}$ are identical or different and having the meaning of $R^3$ and $R^4$ indicated above, $R^{17}$ denotes hydrogen, straight-chain or branched alkenyl having up to 4 carbon atoms or straight-chain or branched alkyl having up to 4 carbon atoms, which is optionally substituted up to 2 times identically or differently by hydroxyl, carboxyl or by straight-chain or branched alkoxycarbonyl having up to 3 carbon atoms, and/or said aryl or heterocycle D or L is optionally substituted by phenyl, pyrimidyl, pyridazinyl, pyridyl, thienyl or furyl, each of which is optionally substituted up to 2 times identically or differently by fluorine, chlorine, bromine, hydroxyl, nitro, carboxyl, trifluoromethyl or by straight-chain or branched alkyl, alkoxy or alkoxycarbonyl each having up to 3 carbon atoms or by a group of the formula($V'_d$)—$NR^{18}R^{19}$, in which d has the meaning of a indicated above and is identical to or different from this, V' has the meaning of V indicated above and is identical to or different from this, $R^{18}$ and $R^{19}$ have the meaning of $R^3$ and $R^4$ indicated above, or D represents a radical of the formula

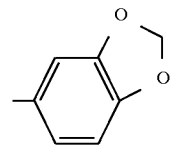

and

E represents a radical of the formula —$CH_2$—Y—Z—, in which

Y denotes a bond or an oxygen or sulphur atom or the —NH group,

Z denotes a straight-chain or branched alkylene chain having up to 4 carbon atoms, or a tautomer or a salt thereof.

4. A method of treating hypertrophy in a patient in need thereof which comprises administering to said patient an amount effective therefor of the compound or a tautomer or salt thereof according to claim 1.

5. A method of treating impotence in a patient in need thereof which comprises administering to said patient an amount effective therefor of the compound or a tautomer or salt thereof according to claim 1.

6. A method of treating incontinence in a patient in need thereof which comprises administering to said patient an amount effective therefor of the compound or a tautomer or salt thereof according to claim 1.

* * * * *